US008874228B2

(12) United States Patent
Phillips et al.

(10) Patent No.: US 8,874,228 B2
(45) Date of Patent: Oct. 28, 2014

(54) INTEGRATED SYSTEM AND METHOD FOR MRI-SAFE IMPLANTABLE DEVICES

(75) Inventors: Michael D. Phillips, Cleveland Heights, OH (US); Mark Joseph Lowe, Greenwood, IN (US)

(73) Assignee: The Cleveland Clinic Foundation, Cleveland, OH (US)

( * ) Notice: Subject to any disclaimer, the term of this patent is extended or adjusted under 35 U.S.C. 154(b) by 2379 days.

(21) Appl. No.: 11/190,779

(22) Filed: Jul. 27, 2005

(65) Prior Publication Data

US 2006/0025820 A1 Feb. 2, 2006

Related U.S. Application Data

(60) Provisional application No. 60/591,099, filed on Jul. 27, 2004.

(51) Int. Cl.
*A61B 5/04* (2006.01)
*A61B 5/055* (2006.01)
*A61N 1/37* (2006.01)

(52) U.S. Cl.
CPC .. *A61B 5/055* (2013.01); *A61N 1/37* (2013.01)
USPC .................................... 607/62; 607/63

(58) Field of Classification Search
USPC .......................................................... 607/62
See application file for complete search history.

(56) References Cited

U.S. PATENT DOCUMENTS

| 5,209,233 | A | * | 5/1993 | Holland et al. ............... 600/412 |
| 5,217,010 | A | | 6/1993 | Tsitlik et al. |
| 5,535,752 | A | | 7/1996 | Halperin et al. |
| 5,669,801 | A | | 9/1997 | Lee |
| 5,928,145 | A | | 7/1999 | Ocali et al. |
| 6,031,375 | A | | 2/2000 | Atalar et al. |
| 6,248,080 | B1 | * | 6/2001 | Miesel et al. ............... 600/561 |
| 6,263,229 | B1 | | 7/2001 | Atalar et al. |
| 6,270,463 | B1 | * | 8/2001 | Morris et al. ............... 600/549 |
| 6,496,714 | B1 | | 12/2002 | Weiss et al. |

(Continued)

FOREIGN PATENT DOCUMENTS

| WO | WO-00/25672 A1 | 5/2000 |
| WO | WO-02/083016 A1 | 10/2002 |
| WO | WO-03/102614 A1 | 12/2003 |

OTHER PUBLICATIONS

Susil, RC, Yeung, CJ, and Atalar, E. Intravascular Extended Sensitivity (IVES) MRI Antennas, Magnetic Resonance in Medicine 2003; 50:383-390.

(Continued)

*Primary Examiner* — Eric D. Bertram
(74) *Attorney, Agent, or Firm* — Tarolli, Sundheim, Covell & Tummino LLP

(57) ABSTRACT

An implantable system includes at least one electrode that is configured to apply a stimulus to surrounding tissue based on a control signal. A control module provides the control signal, such as for controlling application of the stimulus, which can be an electrical stimulus, a chemical stimulus or a combination thereof. A detector is configured to detect a temperature characteristic associated with one or more of the electrode and the surrounding tissue. An output signal is provided based on the detected temperature characteristic. The output signal can be used by an associated diagnostic system to terminate a diagnostic procedure, such as to mitigate heating of the electrode and/or the surrounding tissue.

18 Claims, 4 Drawing Sheets

(56) References Cited

U.S. PATENT DOCUMENTS

| | | | |
|---|---|---|---|
| 6,549,800 B1 | 4/2003 | Atalar et al. | |
| 6,606,513 B2 | 8/2003 | Lardo et al. | |
| 6,628,980 B2 | 9/2003 | Atalar et al. | |
| 6,675,033 B1 | 1/2004 | Lardo et al. | |
| 6,681,135 B1 | 1/2004 | Davis et al. | |
| 6,760,628 B2 | 7/2004 | Weiner et al. | |
| 7,285,118 B1 * | 10/2007 | Lozano | 606/41 |
| 2002/0161421 A1 | 10/2002 | Lee et al. | |
| 2003/0002895 A1 | 1/2003 | Kato et al. | |
| 2003/0028094 A1 | 2/2003 | Kumar et al. | |
| 2003/0040185 A1 | 2/2003 | Jun et al. | |
| 2003/0050557 A1 | 3/2003 | Susil et al. | |
| 2003/0125774 A1 | 7/2003 | Salo | |
| 2003/0144718 A1 | 7/2003 | Zeijlemaker | |
| 2003/0204217 A1 * | 10/2003 | Greatbatch | 607/36 |
| 2004/0199069 A1 * | 10/2004 | Connelly et al. | 600/412 |

OTHER PUBLICATIONS

Roguin A., Zviman MM, Meininger GR, Rodrigues ER, Dickfeld TM, Bluemke DA, Lardo A., Berger RD, Calkins H, and Halperin HR. Modern Pacemaker and Implantable Cardioverter/Defibrillator Systems Can Be Magnetic Resonance Imaging Safe: In Vitro and In Vivo Assessment of Safety and Function at 1.5T, Circulation 2004, 110(5):475-482 (Abstract Only).

* cited by examiner

INTEGRATED SYSTEM AND METHOD FOR MRI-SAFE IMPLANTABLE DEVICES

CROSS-REFERENCE TO RELATED APPLICATION

This application claims the benefit of Provisional Patent Application No. 60/591,099, which was filed on Jul. 27, 2004, and entitled "Integrated system for MRI-safe implantable medical devices" and which is incorporated herein by reference.

BACKGROUND

Various types of electronic devices are implanted in patients to maintain as well as to improve a person's quality of life. Examples of implantable electronics include pacemakers, defibrillators, and neurostimulators. Many implantable electronic devices supply electrical energy via one or more strategically placed electrodes. An implantable pulse generator (IPG) is configured to supply electrical energy to the electrodes. For example, an IPG can be utilized to deliver electrical stimulation for a pacemaker, for spinal cord stimulation, for deep-brain stimulations or stimulation of other neurological paths, such as for treatment of various disorders and diseases.

Magnetic Resonance Imaging (MRI) is a diagnostic technique used to produce high quality images of the interior of the human body to detect diseases and other physiological conditions. Electromagnetic field produced during an MRI procedure can interrupt and/or damage implantable electronic devices. Additionally, the interaction between the electromagnetic fields and the implantable electronics may be harmful to the patient under certain conditions. Accordingly, patients that have implantable electronics may have to forego the valuable benefit of this and other diagnostic techniques.

There are efforts to re-design certain features of implantable electronic devices to effectively shield devices and leads against MRI electromagnetic field gradients that will make Implantable electronic devices MRI-safe. Another approach is to modify the MRI procedure (e.g., modify the electromagnetic fields) in a manner that mitigates the risk of damage to the device and the patient.

SUMMARY

The present invention relates to an implantable system that can be utilized more safely in certain types of diagnostic systems, such as in magnetic resonance imaging systems.

According to one aspect of the present invention provides an implantable system that includes at least one electrode that is configured to apply a stimulus to surrounding tissue based on a control signal. A control module provides the control signal, such as for controlling application of the stimulus, which can be an electrical stimulus, a chemical stimulus or a combination thereof. A detector is configured to detect a temperature characteristic associated with one or more of the electrode and the surrounding tissue. An output signal is provided based on the detected temperature characteristic. The output signal can be used by an associated diagnostic system to terminate a diagnostic procedure, such as to mitigate heating of the electrode and/or the surrounding tissue.

Another aspect of the present invention provides an implantable system that includes a lead system comprising a body portion and at least one electrode attached to the body portion. A transducer is operably connected with the lead system. The transducer is operative to provide a transducer signal that varies as a function of a temperature characteristic associated with at least one of the lead system, the at least one electrode and surrounding tissue. An integrated module is communicatively connected with the lead system via an extension. The integrated module includes a signal generator that provides at least one electrical signal to the at least one electrode via the extension and a detector that is configured to provide a detector signal indicative of the temperature characteristic based on the transducer signal.

Yet another aspect of the present invention provides a system for mitigating risk of injury during diagnostic imaging. The system includes an implantable system that comprises at least one device configured for delivering stimulus to surrounding tissue in a patients body and a control module that controls the delivery of stimulus by the at least one device. The control module is configured to provide an output signal based on a temperature characteristic associated with at least one of the at least one device and the surrounding tissue. An interface is configured to communicatively couple the control module with a diagnostic system via a communications link. The diagnostic system is configured to apply at least one magnetic field (e.g., a varying electromagnetic field and gradient magnetic field). The diagnostic system is also configured to terminate the at least one magnetic field in response to the output signal indicating that the temperature characteristic exceeds a threshold.

DETAILED DESCRIPTION

The present invention relates generally to mitigating risks associated with implantable electronic devices so as to enable use of certain diagnostic and imaging systems, such as magnetic resonance imaging (MRI) machines. The present invention operates by allowing the diagnostic/imaging system to terminate acquisition or scanning in response to detecting heating of the implantable electronic system or surrounding tissue.

Figure 1:
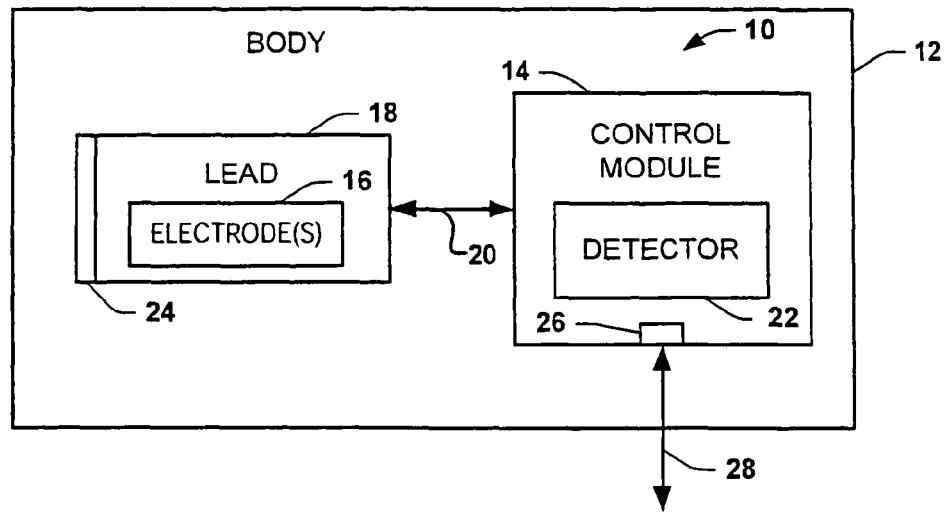
FIG. 1 depicts an example of a block diagram of an MRI safe implantable system according to an aspect of the present invention.

FIG. 1 depicts a diagrammatic representation of an implantable system 10 located within a patient's body 12. It is to be understood and appreciated that the implantable system 10 can correspond to many different types and configurations of implantable electronic systems, such as including pacemakers, defibrillators, and neurostimulators to name a few. Other implantable electronic systems 10 that can implement the present invention include implantable infusion pumps. These and other implantable electronic systems 10 include a control module 14, such as an implantable pulse generator (IPG).

As used herein, the term "IPG" refers to a small device or module that is implantable subcutaneously at a desired location (e.g., below the collarbone or in the abdomen) for applying a desired stimulus to targeted tissue in the patient's body 12. The stimulus may be electrical, chemical or a combination of electrical and chemical. The control module 14 includes a signal generator configured to provide an electrical signal to effect delivery of the stimulus. For example, the signal generator can provide an electrical signal to one or more electrodes 16 implanted at one or more locations where electrical stimulation is desired. The one or more electrodes 16 can be operatively connected to a lead 18, forming part of a lead system.

Those skilled in the art will understand and appreciate various types and configurations of control modules that can be configured in accordance with an aspect of the present invention, including existing designs (both commercially available and proprietary) as well as those that may be developed in the future. Many IPG's include microprocessors and memory for controlling stimulation that is applied by a signal generator component. These and other IPG's can be utilized to treat a variety of different diseases, disorders and/or defects, such as including those relating to the nervous system or cardiovascular system.

The lead 18 can include an elongate body portion (e.g., a thin elongated insulated coiled wire) that includes the one or more electrodes 16 mounted near a distal end thereof. The one or more electrodes 16 are connected to the control module 14 via an appropriately insulated electrically conductive material, such as an extension 20 formed of one or more insulated wires. Where more than one electrode 16 is implemented in the implantable system 10, one or more conductors can be utilized for propagating signals from the signal generator to the respective electrodes. The length of the extension 20 between the control module 14 and the lead 16 can vary according to the particular type of implantable system 10 and its application as well as the size of the patient. The control module 14 typically also includes a power supply, such as a battery, for providing power to the components of the control module 14 to enable operation for extended periods of time (e.g., months or years).

By way of example, for treatment of pain, the electrode 16 can be placed in the spinal column. For pacing of a patient's heart, the electrode 16 may be placed either inside the heart or outside the heart. For treatment of neurological disorders, such as tremors (e.g., due to Parkinson's disease or epilepsy), the electrode(s) 16 can be placed in the brain. Electrical and other stimulation can also be utilized to treat bladder control (e.g., due to urinary incontinence), such as by placing the electrode 16 for supplying stimulation to a sacral nerve.

By way of further example, electrical stimulation of tissue can be implemented by the control module 14 providing electrical pulses to the electrodes 16 according to predetermined stimulation parameters. For instance, the pulses can have amplitudes of from about 0 V to about 20 volts, pulse widths varying from 0.02 to 1.5 milliseconds, and frequency varying from 0 to about 5000 Hz. The appropriate stimulation parameters (e.g., amplitude, frequency, duty cycle) can vary based on treatment desired by a physician or other clinician. It is to be understood that other uses of implantable electronic systems exist and the invention is not limited to the examples of types of devices and treatments listed herein.

The implantable system 10 also includes a detector 22 that is configured to provide an output signal that varies depending upon a temperature characteristic associated with the electrode 16, the lead 18 and/or surrounding tissue in the patient's body 12. The detector 22 can determine whether a heating condition at or near the lead is occurring based on direct temperature measurements or based on indirect temperature measurements made by a transducer 24. It is to be appreciated that the one or more electrodes 16 can be utilized as the temperature transducer 24 by operating the control module in other modes, for example.

As an example of a direct temperature measurement, the transducer 24 can be implemented as a thermocouple or other temperature-sensing element configured to convert thermal energy directly into electrical energy. The thermocouple can be operatively connected to the lead 18, such as may be positioned near a distal end of the lead. The transducer 24 can provide an electrical signal indicative to the control module 14 via the extension 20. The electrical signal from the thermocouple transducer 24 provides an indication of sensed temperature associated with the electrode 16, the lead 18 and/or the surrounding tissue. The detector 22 thus can determine the occurrence of heating based on the electrical signal provided by the transducer 24. For instance, the detector 22 can determine the occurrence of heating by comparing an indication of the sensed temperature relative to a predefined temperature threshold. The predefined temperature threshold can be set, for example, to be about two degrees (Fahrenheit) above a starting or ambient body temperature of the body 12 adjacent the transducer 24. Alternatively, the detector 22 can determine the occurrence of heating based on detecting a change in temperature, as indicated by two or more samples of the electrical signal from the transducer 24.

As an example of an indirect temperature measurement, the detector 22 can also detect heating based on measuring a change in an electrical characteristic associated with the transducer 24. For example, the transducer 24 may be implemented as a length of an electrically conductive wire that extends along or around a portion of the lead 16. The control module can provide a known voltage or current (e.g., DC or RF) to the wire transducer 24 and determine an indication of temperature based on changes in the impedance of the wire transducer 24. The detector 22 can employ the change in measured voltage or current to ascertain a change in impedance that is functionally related (e.g., proportional to temperature). The temperature can then be utilized to determine whether heating associated with the lead 18, the electrode 16, and/or surrounding tissue in the body 12 has occurred.

The detector 22 (alone or in combination with other circuitry in the control module 14) can also detect a heating condition of based on a rate of change in the indication of temperature with respect to time. The indication of temperature may be sensed directly or indirectly via the transducer 24. The rate of change in temperature can correspond to temperature associated with the lead, the electrode, surrounding tissue in the body 12 or any combination thereof. For example, if the rate of change in temperature exceeds a predetermined threshold (e.g., a positive real value), it may be desirable to shut off or terminate selected operation of a corresponding diagnostic system (e.g., terminating application of RF pulses in an MRI system) since the temperature may be rising at a sufficiently high rate to pose a risk the patient or the implantable system 10. Those skilled in the art will understand and appreciate various other means for sensing temperature characteristics associated with the lead 16 or the surrounding tissue in the body 12 that can be utilized in the implantable system 10.

In response to detecting a heating condition, the control module 14 can provide a corresponding output signal. The output signal can be provided to an interface 26 that can be communicated externally from the control module 14 as well as externally to the body 12. For example, the interface 26 can be coupled to a location outside the body via a communications link, indicated at 28. The communications link 28, for example, can be implemented percutaneously as an electrically conductive link (e.g., one or more wires), a wireless link (e.g., radio frequency or inductive coupled), or an optical link (e.g., fiber optic).

The signal provided by the control module 14 via the communications link 28, for example, can be a logic signal (e.g., one or more bits) that indicates whether a temperature threshold has been exceeded. Alternatively or additionally, signal provided by the control module via the communications link 28 can provide an indication of the sensed temperature (e.g., a temperature value) as well as other information about operation of the implantable system 16. An associated diagnostic system (not shown) can monitor the signal provided via the communications link 28 for controlling operation of the diagnostic system based on the signal being provided via the link. For example, an MRI system can be programmed and/or configured to terminate scanning (e.g., by terminating application of radiofrequency (RF) radiation) if the signal received via the link 28 indicates that heating above a predetermined threshold has occurred in the patient's body. The MRI system can also terminate other aspects of operation in response to the signal received via the link 28, including turning off the gradient field. As a result of terminating MRI scanning, possible heating sources from scanning (e.g., heating directly from applied RF pulses and heating currents induced by changing field gradients) can be reduced or eliminated.

Additionally, the control module 14 can be configured to deliver stimulus to the lead system 18 that is synchronized with the operation of the associated diagnostic system. For example, the communications link 28 can provide bi-directional communications, such by configuring the link to include a plurality (e.g., two or more) of communication channels. One or more of the channels can be utilized to transmit an enable signal from the diagnostic system to the control module 14. For example, an enable signal received on a given channel can activate the temperature detection function of the implantable system 10. For the example of an MRI system, the enable signal can be transmitted via a channel of the communications link 28 to operate the temperature detection function mutually exclusively with the radiofrequency transmit portion of the MRI sequence. In this way, the oscillating magnetic fields and magnetic field gradients transmitted by the MRI system will not overlap with the temperature measurement.

By utilizing a bi-directional communications link 28, those skilled in the art will understand and appreciate that other functionality and control features can be utilized for additional synchronization and cooperative functionality between the diagnostic system and the implantable system 10. As one example, the MRI sequence can be controlled as a function of detected temperature associated with the lead 16 such that the diagnostic procedure may continue or be modified as a function of the detected temperature characteristics. The communications link 28 can also be utilized to synchronize stimulation of the adjacent tissue by the electrode 16 with the scanning implemented by the diagnostic system as well as to adjust the programming of the control module 14 for other purposes.

Figure 2:
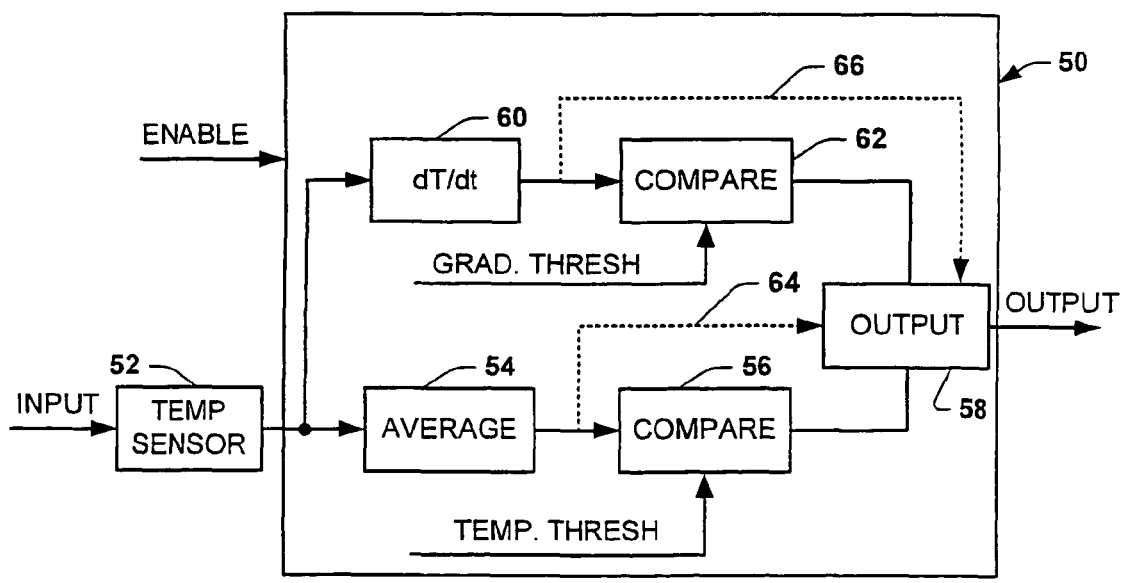
FIG. 2 depicts an example of a detector that can be utilized in an implantable system according to an aspect of the present invention.

By way of further example, FIG. 2 depicts an example of a detection system 50 that can be implemented in an implantable signal generator according to an aspect of the present invention. The detection system 50 can be implemented in hardware, in software (running as executable instructions in a microprocessor) or as a combination of hardware and software. For example, many IPG's include microprocessors and memory that can be programmed to implement various functions. Such microprocessors and memory in an IPG thus can be programmed to implement functionality of the detection system 50 according to an aspect of the present invention.

In the example of FIG. 2, the detection system 50 receives an INPUT signal at a temperature sensor 52. The INPUT signal for example can correspond to a raw analog signal, such as a current or a voltage having a value indicative of a temperature characteristic. The INPUT signal, for example, can be provided by a thermocouple, or correspond to a signal across a wire or other transducer that is operatively connected with a lead of the implantable system. As described with respect to FIG. 1, the INPUT signal thus can provide an indication of a temperature characteristic associated with a lead, an electrode, tissue adjacent the lead or electrode or any combination thereof. The temperature sensor 52 can include circuitry that converts the raw INPUT signal (e.g., voltage or current) to a corresponding normalized signal indicative of the temperature characteristic. For example, the temperature sensor 52 can include an analog-to-digital converter for converting the analog INPUT signal to a corresponding digital indication of the temperature characteristic. The digital indication of temperature can be provided to a microprocessor or other circuitry implementing the temperature detection function.

To mitigate potential fluctuations in the INPUT signal or the temperature, the temperature sensor 52 can provide the indication of temperature to an average block 54. The average block 54, for example, can be implemented as a filter or as an accumulator, such as by storing a plurality of samples of the temperature sensor value and averaging the stored samples to provide an average indication of the temperature over a time period (e.g., about ten samples acquire over milliseconds).

A comparator 56 compares the average indication of temperature with a corresponding temperature threshold. The temperature threshold can be programmed or set to a value that enables the detection system 50 to detect potential heating associated with a lead, an electrode and/or tissue adjacent the lead or electrode. The comparator 56 provides a comparator output signal to output circuitry 58 based upon the comparison of the average temperature relative to the temperature threshold.

The output circuitry 58 provides an OUTPUT signal based on the comparator output signal. For instance, the output circuitry 58 can include a driver or other circuitry that drives an output port of an implantable control module with a logic signal (e.g., a binary signal) that indicates whether a heating condition exists, such as based on the threshold being exceeded. As described herein, the OUTPUT signal can be detected by an associated diagnostic system via a corresponding communications link.

As one example, the temperature threshold can be programmed prior to beginning a diagnostic procedure in which it is desirable to detect heating. For example, the temperature threshold can be programmed prior to initiating the diagnostic procedure based on an initial set of one or more temperature measurements (e.g., provided by the average block 54). The initial temperature measurement provides a baseline for establishing a corresponding temperature threshold. That is, the temperature threshold can be set to a temperature value that is higher (e.g., about two degrees higher) than the baseline.

In addition to detecting heating due to an absolute temperature condition, the detection system 50 can also be utilized to detect a rate of change in temperature. In this regard, the detection system 50 may include a differentiator (dT/dt) 60 that differentiates the indication of temperature from the temperature sensor 52 with respect to time. Those skilled in the art will understand and appreciate various approaches that can be employed to implement the differentiation (hardware and/or software). The differentiator 60 thus provides an indication of the change in temperature with respect to time.

A comparator 62 evaluates the change in temperature with respect to time relative to a gradient rise-time threshold to determine whether the change in temperature with respect to time is too high. The gradient rise-time threshold can be set based on empirical testing as well as based on simulation so as to detect a potential heating condition. The comparator 62 provides a corresponding comparator output signal to the output circuitry 58. The output circuitry 58 thus can provide the OUTPUT signal based on one or both of the comparators 56 and 62 indicating a potential heating condition.

Additionally or alternatively, the output circuitry 58 can be configured to provide the OUTPUT as including a plurality of outputs (e.g., a multi-channel output). For example, the average block 54 can provide an indication of the average temperature directly to the output circuitry 58, as indicated at 64. In this way, the OUTPUT signal can include an indication of the average temperature (e.g., over about 10 samples) that can be utilized by the associated diagnostic system for controlling operation thereof. Additionally or alternatively, the differentiator 60 can provide the output circuitry 58 with an indication of the rate of change in temperature, as indicated at 66. Thus, the OUTPUT signal can provide an indication of the rate of change in temperature that can be used by the diagnostic system for controlling operation thereof.

As a further example, the detection system 50 may also receive an ENABLE signal to enable operation of the detection system. For instance, the ENABLE signal can be provided by the associated diagnostic system or other device that is communicatively coupled to a control module implementing the detector system 50. The ENABLE signal, for example, can be provided for enabling temperature detection intermittently, such as at predefined intervals that can be synchronized with the operation and sequencing of the diagnostic system. As described herein, the ENABLE signal and the OUTPUT signal can be communicated via an appropriate communications link.

Figure 3:
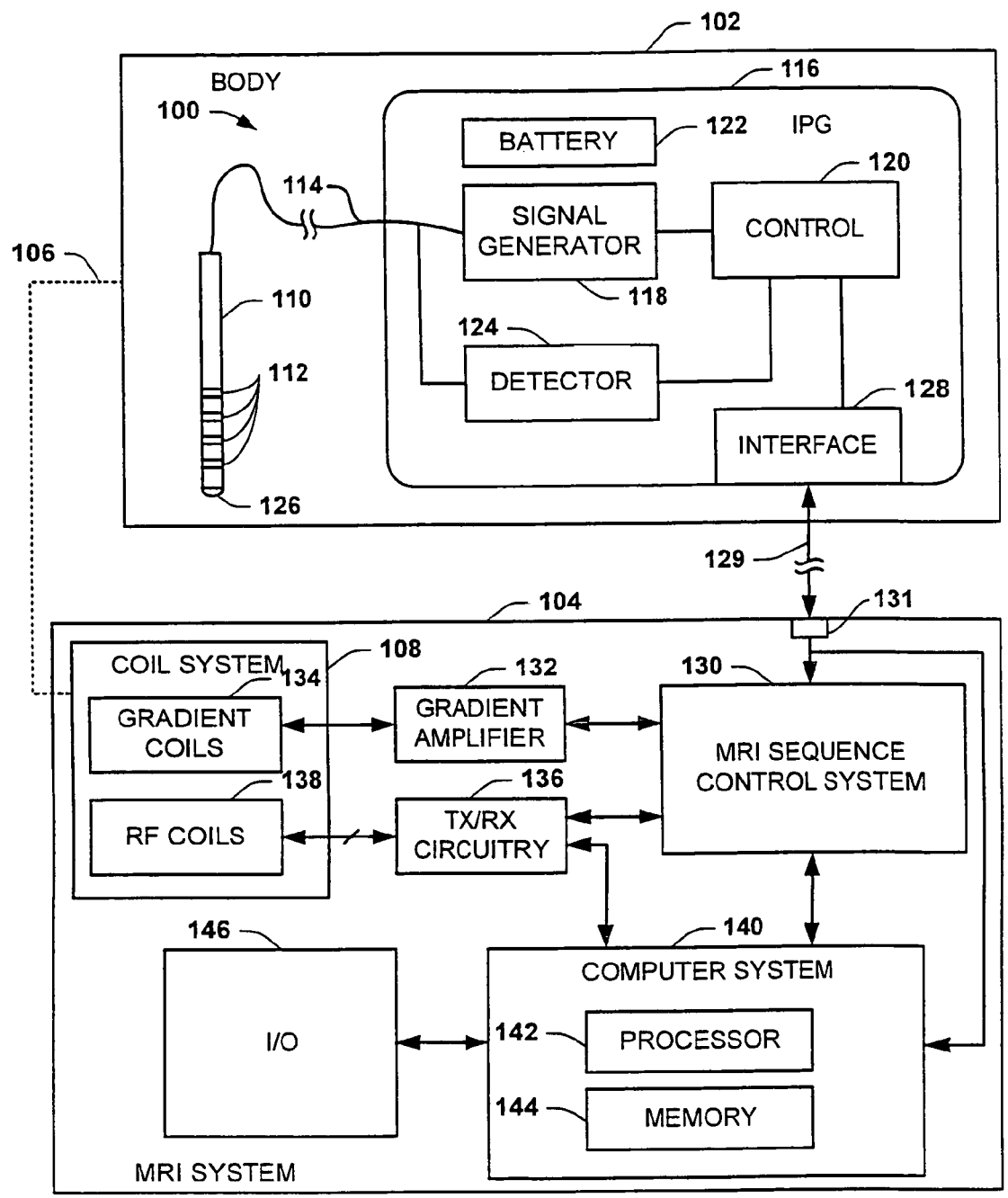
FIG. 3 depicts an example of an MRI safe implantable system implemented in conjunction with an MRI system according to an aspect of the present invention.

FIG. 3 depicts an example of an integrated implantable system 100 that is implanted within a patient's body 102 in the context of an MRI system 104 operative to implement a diagnostic procedure on the patient. For purposes of simplicity of explanation, a dotted line 106 is utilized to show the relationship of the body 102 (or at least a portion thereof) positioned within a coil system 108 of the MRI system 104. Those skilled in the art will understand and appreciate various types of MRI systems 104 as well as other types of diagnostic systems that can be implemented in accordance with an aspect of the present invention.

The implantable system 100 includes one or more leads 110 that can be positioned at strategic locations in the body 102 according to the treatment and function for which the system 100 is being utilized. As described herein, the lead 110 can be implanted in a patient's brain (e.g., for neurostimulation) in or in contact with a patient's heart (e.g., for pacemaker usage or defibrillator usage) or the lead(s) 110 can be implanted at or near a patient's spine (e.g., for pain control) or the lead 110 can be implanted at other locations for other purposes. The lead 110 includes one or more electrodes 112 that are electrically coupled with an IPG 116 via an extension 114. The extension 114 can include an electrically conductive wire for each of the respective electrodes. The extension 114 further can include an additional wire or other means for communicating temperature information between a temperature transducer of the lead 110 and the IPG 116 (e.g., inductive coupling, capacitive coupling, fiber optic and the like).

The IPG 116 includes a signal generator 118 that is configured to provide appropriate pulses or other signals to the electrodes 112. A control system 120 controls the signal generator 118 to deliver appropriate electrical energy to the electrodes. The control system 120 can also be employed to control the lead 110 or other devices to dispense a chemical stimulus (e.g., pharmacological or genetic) to the patient's body 102. Depending upon the type of IPG 116 appropriate sensors (not shown) can also be utilized to sense a condition of the patient for which stimulation is required.

Because the implantable system 110 is implanted within the body 102, the IPG 116 also includes a battery 122 for providing power to the components of the IPG. The IPG 116, for example, can be implanted in the chest near the patient's collar bone or at other suitable locations. The IPG 116 also includes a detector 124 that is operative to detect a heating condition, such as may be associated with the lead 110, the electrodes 112, surrounding tissue or any combination thereof. For example, one or more transducers (e.g., see FIGS. 4 and 5) can be connected to or integrated into the lead 112, such as near a distal tip 126 thereof. The detector 124 can be coupled with the transducer via one or more wires implemented in the extension 114 that interconnects the IPG 116 and the lead 110. The detector 124, for example, can provide a small current to the transducer and monitor the signal to ascertain the occurrence of a heating condition within the body 102. Alternatively, the transducer can provide an electrical signal that varies as a function of temperature. Additionally, multiple transducers can be utilized, each of which may be the same or different type of transducer that cooperate to enable the detector 124 to ascertain the occurrence of the heating condition.

The control system 120 can include logic that determines the occurrence of a heating condition such as in response to pulsed RF radiation applied by the MRI system 104. The logic can be implemented in hardware, in software, or a combination of hardware and software. The control system 120 can provide a corresponding output signal indicating the occurrence of a heating condition to the MRI system via an interface 128. The interface 128 can be integrated into the IPG so as to be accessible through a portion of the body 102 for establishing a percutaneous communications link 129 between the IPG and the MRI system 104. For example, the communications link 129 may be an electrically conductive link, a wireless link or an optical link.

As an example, can be configured to a portion of the housing of the IPG 116 overlying the interface 128 permits penetration through the material yet still maintains a substantially hermetic barrier in the housing. A needle or other elongated device thus can penetrate through the compliant portion of the IPG housing and communicatively couple with the interface 128 to provide for communications between the IPG 116 and the MRI system 104. The interface 128 can be an electrical-to-electrical interface, an electrical-to-optical interface, or an optical-to-optical interface. Additionally or alternatively, the interface may provide a wireless link, such as by inductive coupling or RF telemetry. The control system 120 thus provides the output signal to the MRI system, such as in response to detecting a heating condition (see, e.g., FIG. 2). The MRI system 104 is operative to terminate an MRI sequence in response to the output signal provided by the IPG 116 via the communications link 129.

The communications link 129 can connect to a corresponding interface 131 of the MRI system 104. The interface 131, for instance, corresponds to a port or other connection through which the MRI system 104 can receive the output signal. For example, the interface 131 may correspond to an extra or auxiliary channel of a multi-channel coil system 108 or to an input of a physiological monitoring system of the MRI system. The protocol and type of signals can be any known or proprietary format, which may vary according to the manufacturer of the MRI system 104. The communications link 129 as well as the respective interfaces 128 and 131 can be bi-directional or unidirectional.

By way of further example, the MRI system 104 includes an MRI sequence control system 130 that is configured to control the MRI sequence. For example, the MRI sequence control system 130 can provide control signals to a gradient amplifier 132 that supplies variable current to an arrangement of gradient coils 134. The gradient coils 134 are arranged to establish a gradient field for implementing MRI imaging based on the current provided by the gradient amplifier 132. The gradient coils can be formed of a set of gradient coils along transverse axes (e.g., the x, y, and z directions), each of which is controlled by the MRI sequence control system 130 via current applied by the gradient amplified system 132.

The MRI sequence control system 130 can also control transmit and receive (TX/RX) circuitry 136 via respective transmit and receive paths. The TX/RX circuitry 136 can generate an oscillating magnetic field via application of RF current to RF coils 138 of the coil system 108. The RF coils 138, for example, apply RF pulses (generating an oscillating magnetic field) to the patient's body 102 according to electrical current provided by an RF power amplifier of the TX/RX circuitry 136. The TX/RX circuitry 136 can also employ the RF coils 138 to convert a precessing magnetism to electrical signals, which are provided to a computer system 140 via the receive path.

The computer system 140 controls and links the various components of the MRI system 104. The computer system 140 is programmed and configured for storing data acquired during the MRI procedure sequences as well as for constructing an image based on the data acquired from the TX/RX circuitry 136. The computer system 140 thus includes a processor 142 for executing instructions as well as appropriate memory 144 for storing the executable instructions and the acquired data. One or more I/O devices, indicated at 146, can also be connected with the computer system 140 to provide means for interacting (e.g., human machine interface and display) with the MRI system 104.

According to an aspect of the present invention, the MRI system 104 is operative to control the RF pulses applied by the coil system 108 in response to detecting heating associated with the implantable system 100. For example, the MRI sequence control system 130 can terminate an ongoing MRI sequence in response to the output signal from the implantable system 100 indicating potential heating of part of the implantable system or surrounding tissue in the patient's body 102. One or more selected aspects of the MRI sequence can be terminated, for example, including termination of RF pulses being applied by the RF coils 138. For example, the RF power amplifier of the TX/RX circuitry 136 can be turned off or the transmit path can otherwise be interrupted. Other aspects of the MRI sequence (e.g., turning off the magnetic field gradient) can also be terminated. Such control can be implemented by the MRI sequence control system 130 or by the computer system 140 in response to the signal received via the communications link 129. As mentioned above, the communications link 129 can provide a logic signal that indicates heating has exceeded a threshold. Alternatively, raw electrical signals and/or temperature information can be provided via the communications link 129 based on which the MRI sequence can be terminated or adjusted to reduce potential heating.

As an alternative example, the communications link 129 can also be coupled with the computer system 140 via the interface 131. The acquisition software or sequence code running in the processor 142 computer system 140 can include a routine that monitors the value of signal transmitted over the communications link 129 by the IPG 116. The acquisition software and sequence code thus can terminate the image acquisition process by terminating the applied RF pulses in response to the output signal from the implantable system 100 indicating a potential heating condition.

As mentioned above, the communications link 129 may be bi-directional. Accordingly, the MRI system 104 or other devices can be utilized to program the temperature detection function implemented by the IPG 116. For example, prior to initiating an MRI sequence, the computer system 140 can calibrate or program the temperature detection function, such as by setting one or more temperature thresholds. In one example, one or more temperature measurements can be made prior to initiating the MRI sequence to determine a baseline or starting temperature value. The determination of the baseline temperature can be made by the control system 120 of the IPG 116 or it can be made by the computer system 140 based on information provided over the communications link. The one or more thresholds can be then set based on the baseline temperature, such as corresponding to a predetermined number of degrees greater than the baseline temperature (e.g., approximately two degrees Fahrenheit greater). Those skilled in the art will understand and appreciate that other temperature thresholds can be utilized. The threshold and/or the starting value can be programmed in the IPG 116 for use in detecting the potential heating condition.

When the communications link 129 is bi-directional, the MRI system 104 can also provide a synchronization signal that indicates when the IPG 116 should activate the temperature detection function. For example, the MRI system 104 can provide an enable signal to activate the IPG 116 via the communications link 129 when the RF coils 138 do not apply RF energy to the patient's body 102 as well as when the gradient amplifier 132 does not provide current to the gradient coils 134 for establishing the gradient field. Alternatively or additionally, the MRI system 104 can provide a disable signal for deactivating the temperature detection function of the IPG 116 during times when the RF coils 138 are activated to apply RF energy or when the gradient amplifier 132 is controlled to apply the gradient magnetic field.

Figure 4:
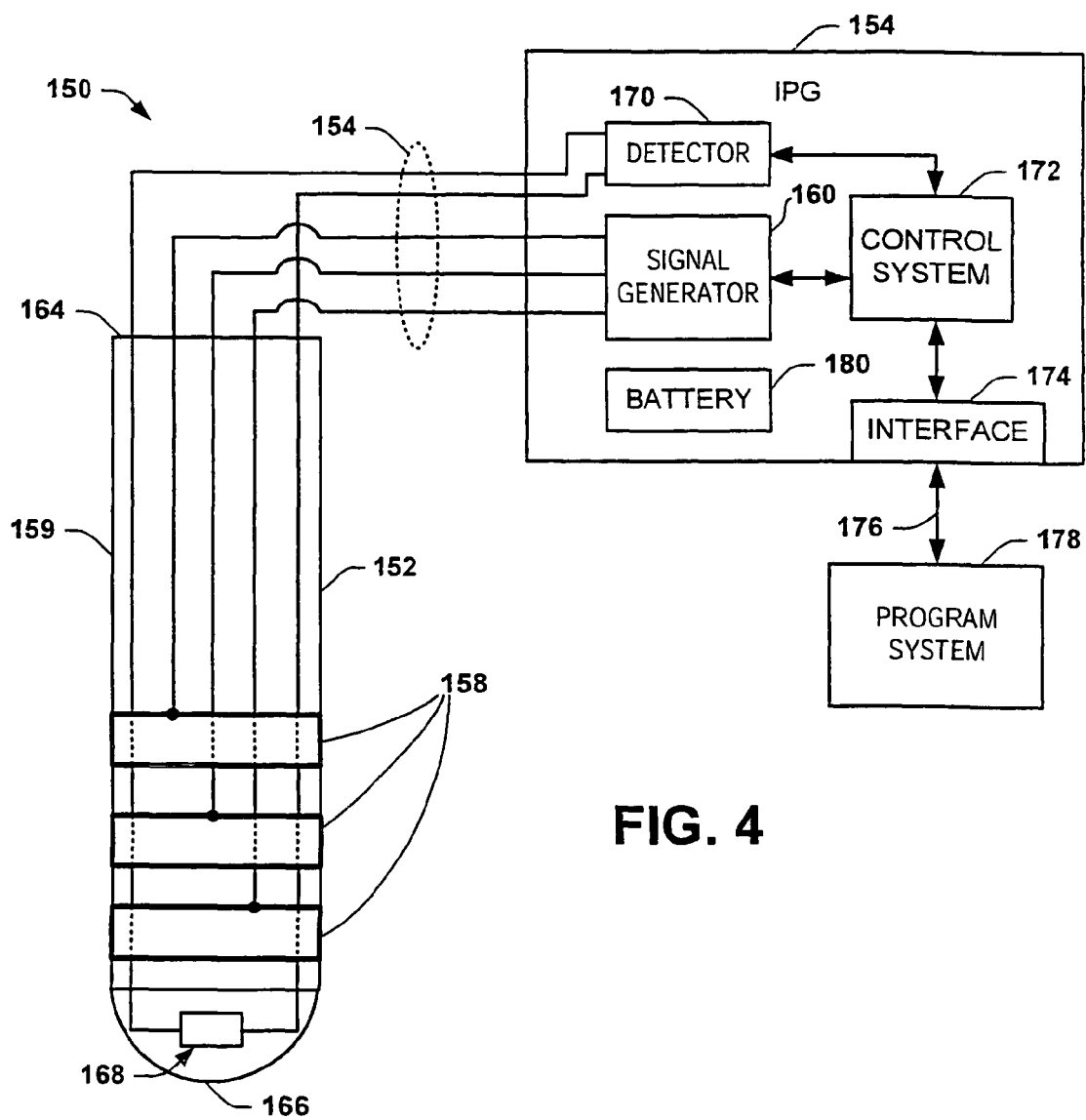
FIG. 4 depicts an example of one type of MRI safe implantable according to an aspect of the present invention.
Figure 5:
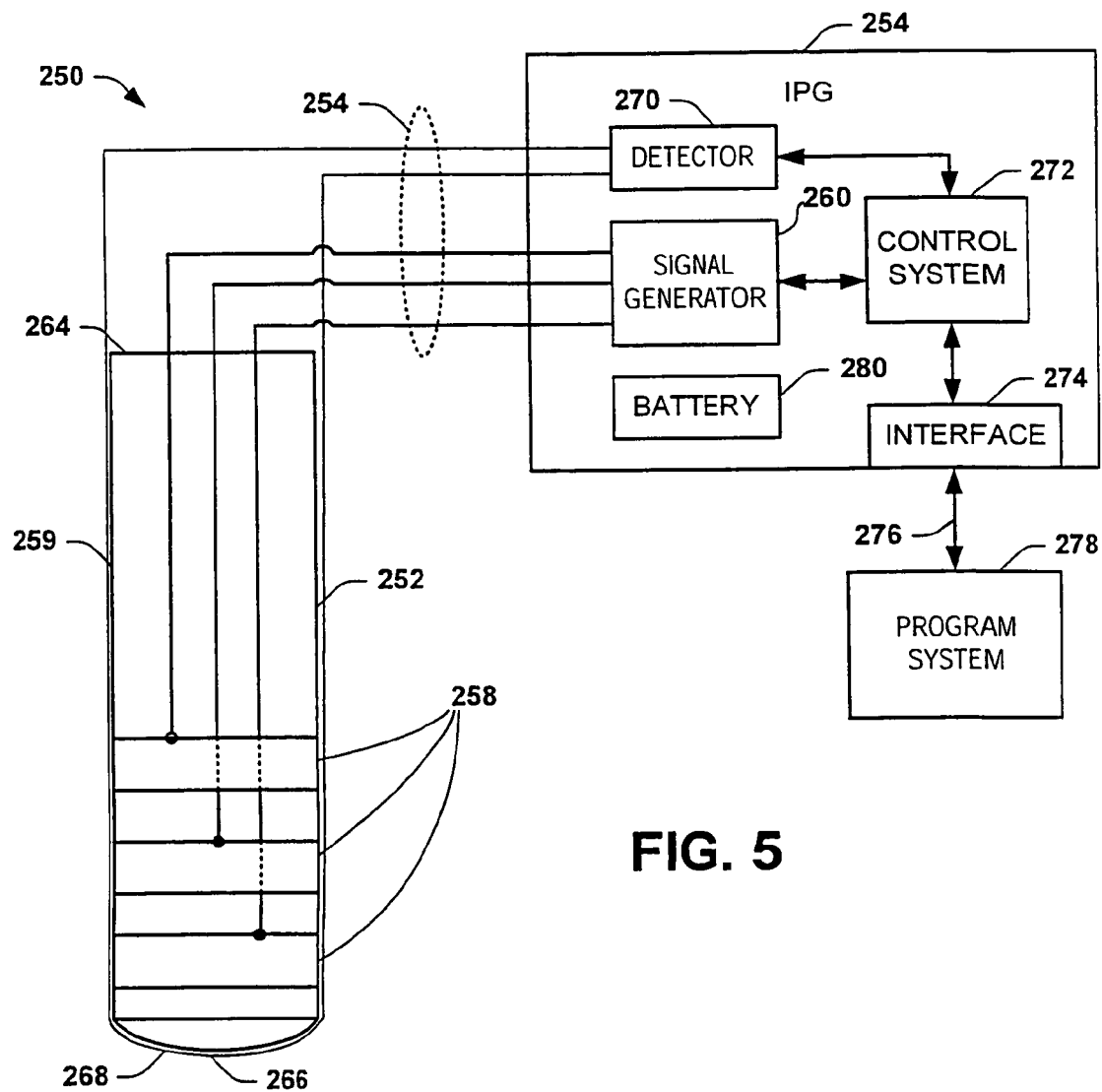
FIG. 5 depicts an example of another type of MRI safe implantable device according to an aspect of the present invention.

FIGS. 4 and 5 depict examples of different types of implantable stimulation systems that can be implemented in according to an aspect of the present invention. Referring to FIG. 4, the implantable stimulation system 150 includes a lead 152 that is communicatively coupled with an IPG 154 via an appropriate extension 156. The lead 152 includes a plurality of electrodes 158 that extend circumferentially around at least a portion of an elongated body portion 159 of the lead. Each of the electrodes 158 is connected with a signal generator 160 of the IPG 154. The signal generator 160 is configured to provide electrical stimulation (e.g., in the form of current or voltage) to the electrodes 158. The elongated body portion 159 defines a sidewall of the lead 152 that extends between a proximal end 164 and terminates at a distal end 166. In the example of FIG. 4, the lead body portion 159 has a generally fixed diameter, although a fixed diameter is not required. Those skilled in the art will understand and appreciate that other arrangements and configurations of electrodes and leads can be utilized according to an aspect of the present invention. As mentioned above, various types of electrodes can also be implemented without a corresponding lead.

A transducer 168, such as a thermocouple or other device that provides an electrical signal as a function of temperature, is implemented near the distal end 166 of the lead 152. For example, the transducer 168 can be encapsulated or potted within a substantially thermally conductive material. Alternatively, the transducer can be exposed to surrounding tissue. The transducer 168 is electrically connected with a detector 170 of the IPG 154. The transducer 168 thus can provide an indication of the temperature of surrounding tissue as well as the temperature of the lead 160, which is received by the detector 170. For certain types of transducers, the transducer 168 may provide the temperature signal in response to a signal from the detector or a control system 172 of the IPG 154.

The detector 170 provides an indication of detected temperature to the control system 172. The detector 170, for example, can include analog-to-digital converter for converting an analog indication of temperature to an appropriate digital value. The control system 172 can include a microprocessor and memory for implementing an appropriate heating detection algorithm, such as described herein. Alternatively, the heating detection function can be implemented by hardware implemented in the IPG. The control system 172 can communicate the temperature information or an indication of a potential heating condition to an interface 174, which can be accessed externally from the IPG 154. As an example, the interface 174 can be accessed via a communications link 176. After the implantable system 100 has been implanted in a patient, the communications link 176 can be percutaneous.

By way of further example, after the system 150 has been implanted in a patient, a program system 178 can be utilized to program the IPG 154 via the communications link 176. For instance, the program system 178 can set one or more temperature thresholds utilized by the temperature detection function of the IPG, such as preceding a diagnostic routine (e.g., MRI imaging) that may cause potential heating of the lead 152, the electrodes 158 and/or surrounding tissue. The programming of the thresholds prior to the diagnostic routine is advantageous as the resistance of the transducer and condition of the surrounding tissue in which the lead 152 is implanted can vary from patient to patient as well may vary according to particular application in which the implantable system 150 is being utilized. Additionally, the program system 178 can be connected to program other operating parameters of the IPG 154 to provide a desired stimulation to the patient in which it is implanted. As a further example, the program system 178 can be implemented as computer executable instruction running in a computer system of the diagnostic system or it can be a separate, stand-alone unit.

Since the IPG 154 is implanted subcutaneously in a patient, the IPG includes a battery (or other power supply) for providing electrical energy for powering the IPG, including the temperature detection function. The percutaneous communications link 176 with the interface 174 can provide means for recharging the battery and thereby reducing the frequency by which the IPG 154 may need to be replaced. Other adjustments and programming and maintenance and diagnostic functions of the IPG can also be implemented via the communications link 176 with the interface 172.

FIG. 5 depicts another example of an implantable system 250 in which identical reference numbers, increased by adding 100 refer to parts and components previously identified in FIG. 4. Additional information about various components of the implantable system 250 thus may be obtained by reference to the corresponding description of FIG. 4.

The system 250 includes a temperature transducer 268 implemented as an electrically conductive element, such as a wire. For example, the wire extends longitudinally at or near an exterior surface of at least part of the body portion 259. In the example of FIG. 5, the wire extends from the proximal end to 264 of the lead 252 along the body portion 259 and over the distal end 266 of the lead and then along the substantially diametrically opposed side surface of the lead 252. The transducer 268 provides a low resistance path element through which a signal can be applied for determining an indication of temperature for the lead 252 as well as for surrounding tissue.

For example, the detector 270 (or other circuitry in the IPG 254) is configured to provide electrical current signal through the transducer 268 and detect a corresponding voltage. The current signal can be applied during part of an MRI sequence (e.g., when no gradient field is being applied) such that the detector 270 can detect an indication of temperature associated with the lead. Since the impedance of the transducer 268 varies as a function of temperature, the detector 270 can provide a signal to the control system that varies as a function of temperature perceived by the transducer 268 along the entire length of the lead. The control system 272 can provide a corresponding output signal that indicates whether the detected temperature exceeds a predetermined threshold.

Those skilled in the art will understand and appreciate various different types of transducers that can be implemented into the implantable system for detecting temperature. While examples of FIGS. 4 and 5 demonstrate transducers associated with the lead of the implantable system 150 and 250, it is to be understood and appreciated that one or more detectors can also be integrated into the IPG itself or any other part of the implantable system. In this way, potential heating for any part of the implantable system 150 and 250 can be determined and utilized to control operation (e.g., to disable or stop scanning) of an associated diagnostic system.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the spirit and scope of the appended claims.

What is claimed is:

1. An implantable system, comprising:
  a lead system comprising a body portion and at least one electrode attached to the body portion, the lead system being configured for implantation in a patient;
  a transducer operably connected with the lead system, the transducer being operative to provide a transducer signal that varies as a function of a temperature characteristic of surrounding tissue;
  an integrated implantable module communicatively connected with the lead system via an extension, the module comprising:
    a signal generator that provides at least one electrical signal to the at least one electrode via the extension; and
    a detector configured to provide a detector signal indicative of the temperature of the surrounding tissue based on the transducer signal; and
  an interface configured to communicatively couple the integrated implantable module with a diagnostic system that is located external to the integrated implantable module via a communications link, wherein the diagnostic system is a Magnetic Resonance Imaging (MRI) system.

2. The implantable system of claim 1, further comprising a control system configured to control the signal generator to provide the at least one electrical signal, the control system also providing an output signal in response to determining that the temperature characteristic exceeds a temperature threshold based on the detector signal.

3. The implantable system of claim 2, wherein the temperature threshold is programmable.

4. The implantable system of claim 1, wherein the transducer comprises a thermocouple located adjacent a distal end of the of the body portion.

5. The implantable system of claim 1, wherein the detector further comprises:
   a comparator that provides a first comparator signal based on comparison of the indication of a temperature characteristic relative to a predetermined threshold;
   a second comparator that provides a second comparator signal based on comparison of a rate of change in temperature associated with at least one of the at least one electrode and the surrounding tissue relative to a predetermined temperature threshold, the rate of change in temperature being determined as a function of the indication of a temperature characteristic provided by the detector; and
   the integrated implantable module providing an output signal based on at least one of the first comparator signal and the second comparator signal.

6. An implantable system, comprising:
   a lead system comprising a body portion and at least one electrode attached to the body portion;
   a transducer operably connected with the lead system, the transducer being operative to provide a transducer signal that varies as a function of a temperature characteristic of surrounding tissue;
   an integrated module communicatively connected with the lead system via an extension, the module comprising:
      a signal generator that provides at least one electrical signal to the at least one electrode via the extension; and
      a detector configured to provide a detector signal indicative of the temperature of the surrounding tissue based on the transducer signal; and
   an interface configured to communicatively couple the integrated module with a diagnostic system that is located external to the integrated module via a communications link, the diagnostic system terminating at least application of radiofrequency pulses in response to a signal received via the communications link indicating that the temperature characteristic exceeds a temperature threshold.

7. The implantable system of claim 6, wherein the communications link comprises one of an electrically conductive link, a wireless link and an optical link.

8. An implantable system, comprising:
   a lead system that includes at least one electrode operatively connected to an elongate body portion of the lead system, the at least one electrode configured to apply a stimulus to surrounding tissue based on a control signal;
   an implantable control module that provides the control signal;
   an extension that electrically connects the at least one electrode of the lead system with the implantable control module; and
   an implantable transducer connected with the lead system, the implantable transducer being communicatively coupled with the implantable control module and configured for sensing temperature characteristics associated with the surrounding tissue and providing a temperature signal that varies as a function of the sensed temperature of the surrounding tissue,
   the implantable control module detecting a temperature characteristic of the surrounding tissue and providing an output signal based on the temperature signal, the output signal being provided to a diagnostic system that is located external to the implantable control module; and
   an interface configured to communicatively couple the implantable control module with the diagnostic system via a communications link, the diagnostic system controlling at least application of radiofrequency pulses based the output signal provided by the implantable control module indicating that the temperature characteristic exceeds a temperature threshold.

9. The implantable system of claim 8, wherein the implantable transducer is located adjacent a distal end of the of the elongate body portion.

10. The implantable system of claim 8, wherein the implantable transducer comprises a thermocouple.

11. The implantable system of claim 8, wherein the communications link comprises one of an electrically conductive link, a wireless link and an optical link.

12. The implantable system of claim 8, wherein the implantable control module further comprises:
   a comparator that provides a first comparator signal based on comparison of an average indication of detected temperature associated with at least one of the at least one electrode and the surrounding tissue relative to a predetermined temperature threshold; and
   output circuitry that provides the output signal based on the first comparator signal.

13. An implantable system, comprising:
   a lead system comprising a body portion and at least one electrode attached to the body portion, the lead system being configured for implantation in a patient;
   a transducer connected with the lead system, the transducer being operative to provide a transducer signal that varies as a function of temperature of a surrounding tissue environment;
   an integrated implantable module communicatively connected with the lead system, the module comprising:
      a signal generator that provides at least one electrical signal to the at least one electrode;
      a detector configured to provide a detector signal indicative of the temperature characteristic based on the transducer signal; and
      a control system configured to control the signal generator to provide the at least one electrical signal, the control system also providing an output signal to an imaging system that is external to the integrated implantable module in response to determining that the temperature characteristic of the surrounding tissue environment exceeds a temperature threshold based on the detector signal.

14. The implantable system of claim 13, further comprising an interface configured to communicatively couple the integrated implantable module with the imaging system via a communications link, the imaging system terminating at least application of radiofrequency pulses based on the output signal provided by the control module indicating that the temperature characteristic exceeds the temperature threshold.

15. The implantable system of claim 13, wherein the temperature threshold is programmable.

16. The implantable system of claim 13, wherein the detector further comprises:
- a comparator that provides a first comparator signal based on comparison of an average indication of detected temperature associated with at least one of the at least one electrode and the surrounding tissue relative to a predetermined temperature threshold; and
- output circuitry that provides the output signal based on the first comparator signal.

17. An implantable system, comprising:
- a lead system comprising a body portion and at least one electrode attached to the body portion;
- a transducer operably connected with the lead system, the transducer being operative to provide a transducer signal that varies as a function of a temperature characteristic associated with at least one of the lead system, the at least one electrode and surrounding tissue;
- an integrated module communicatively connected with the lead system via an extension, the module comprising:
  - a signal generator that provides at least one electrical signal to the at least one electrode via the extension; and
  - a detector configured to provide a detector signal indicative of the temperature characteristic based on the transducer signal, wherein the detector is configured to receive an enable signal from the diagnostic system via the communication link to enable operation of the detector; and
  - an interface configured to communicatively couple the integrated module with a diagnostic system via a communications link, the diagnostic system terminating at least application of radiofrequency pulses in response to a signal received via the communications link indicating that the temperature characteristic exceeds a temperature threshold.

18. The implantable system of claim 17, wherein the enable signal is provided by the diagnostic system to synchronize operation of the detector with operation of the diagnostic system.

* * * * *